United States Patent [19]

Bollens et al.

[11] Patent Number: 5,026,910
[45] Date of Patent: Jun. 25, 1991

[54] POLYFLUOROALKYL NITROGEN COMPOUNDS, PROCESSES FOR THEIR PREPARATION AND THEIR USE

[75] Inventors: Eric Bollens, Nice; Francois Szonyi, Monaco; Aime Cambon, Nice, all of France

[73] Assignee: Societe Atochem, Puteaux, France

[21] Appl. No.: 526,992

[22] Filed: May 22, 1990

[30] Foreign Application Priority Data

May 22, 1989 [FR] France ................................. 8906639

[51] Int. Cl.$^5$ .................. C07C 335/10; C07C 385/08
[52] U.S. Cl. ....................... 564/27; 558/302; 558/413; 558/418; 558/419; 558/422; 558/446; 558/452; 560/13; 560/18; 560/147; 560/150; 562/426; 562/430; 562/432; 562/556; 564/29; 564/30; 564/252
[58] Field of Search .............................. 564/30, 27, 29

[56] References Cited

U.S. PATENT DOCUMENTS

| | | | |
|---|---|---|---|
| 3,174,988 | 3/1965 | Fawcett et al. | 558/17 |
| 3,882,114 | 5/1975 | Kalopissis et al. | 564/30 |
| 4,097,605 | 6/1978 | Fancher | 564/30 |
| 4,487,783 | 12/1984 | Grohe et al. | 564/30 |

FOREIGN PATENT DOCUMENTS

| | | |
|---|---|---|
| 0030092 | 6/1981 | European Pat. Off. . |
| 0304402 | 2/1989 | European Pat. Off. ............. 564/27 |
| 0254578 | 3/1988 | Fed. Rep. of Germany ........ 564/27 |
| 2195678 | 3/1974 | France . |
| 0127414 | 11/1978 | Japan ..................................... 564/30 |
| 59-211663 | 2/1984 | Japan ..................................... 564/30 |
| 1189870 | 4/1970 | United Kingdom . |

OTHER PUBLICATIONS

Inteanat Jour. of Pharmceutics, vol. 31, 1986, pp. 209-223, Elsevier Science Pubs. B.V.; A.L. J. DeMeere et al.: "Local Composition Models in Pharma. Chem. II, Differentiation of Hydrophobic Fragmental Constants", p. 213, TB. 2, Comp. No. 6.

Primary Examiner—Glennon H. Hollrah
Assistant Examiner—Susan P. Treanor
Attorney, Agent, or Firm—Morgan & Finnegan

[57] ABSTRACT

The invention relates to polyfluoroaklyl nitrogen compounds of general formula:

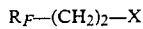

in which X denotes an isothiocyanate —N=C=S, carbodiimide —N=C=N(CH$_2$)$_2$—R'$_F$ or thiourea —NH—CS—A group, A denoting an optionally substituted amino group, and each of the symbols R$_F$ and R'$_F$ denotes a perfluoroalkyl radical.

These compounds, prepared from the corresponding axides R$_F$(CH$_2$)$_2$N$_3$ or amines R$_F$(CH$_2$)$_2$NH$_2$, can be used as surface-active agents or precursors of such agents.

3 Claims, No Drawings

POLYFLUOROALKYL NITROGEN COMPOUNDS, PROCESSES FOR THEIR PREPARATION AND THEIR USE

FIELD OF THE INVENTION

The present invention relates to the field of polyfluoro compounds and its subject is more particularly polyfluoroalkyl nitrogen compounds which can be applied especially as surface-active agents or as precursors of such agents.

BACKGROUND OF THE INVENTION

Many fluorine-containing surfactants are already known and, in particular, quaternary ammonium salts in which a perfluorinated radical is linked to the quaternary ammonium group (for example trialkylammonium or pyridinium) by a bridge whose nature has a great influence on the application properties. This bridge can be very simple, for example $CH_2$ or $C_2H_4$ (U.S. Pat. No. 2,727,923 and French patent No. 1,588,482) or more complex, for example $-C_2H_4SO_2NH(CH_2)_3$ (French patent No. 2,084,888), $-C_2H_4S(CH_2)_3$-$OCH_2CH(OH)CH_2$ (European patent No. 256,980), or the like.

DETAILED DESCRIPTION OF THE INVENTION

The subject of the present invention is now a new group of polyfluoro compounds which can be represented by the general formula:

$$R_F-(CH_2)_2-X$$

in which X denotes the isothiocyanate group $-N=C=S$, a carbodiimide group $-N=C=N(CH_2)_2-R'_F$ or a thiourea group $-NH-CS-A$, A denoting an optionally substituted amino group, and the symbols $R_F$ and $R'_F$ may be identical or different and each denotes a linear or branched perfluoroalkyl radical containing from 2 to 16 carbon atoms, preferably 4 to 12.

When the symbol X denotes a thiourea group $-NH-CS-A$, the group A is advantageously chosen from groups (A1) to (A6) of following formulae:

(A1) $-NH_2$

(A2)

(A3)

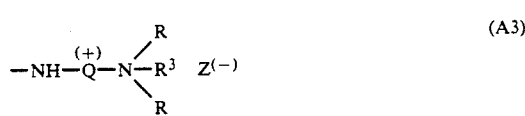
(A4)

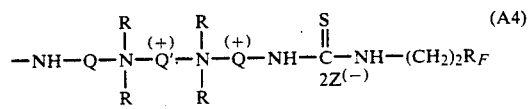
(A5)

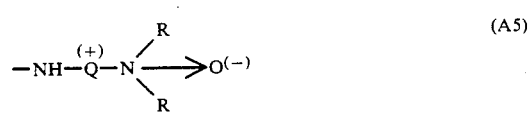
(A6)

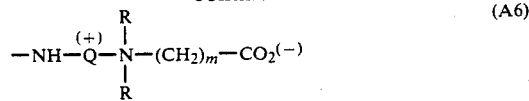

where:

M is equal to 1 or 2, each of Q and Q', which are identical or different, denotes an alkylene bridge of 2 to 8 carbon atoms, R denotes an unsubstituted linear alkyl radical containing from 1 to 4 carbon atoms, $R^1$ denotes a linear or branched alkyl radical containing from 1 to 18 carbon atoms and optionally substituted, an optionally substituted aryl or aralkyl radical, an allyl, methallyl or propargyl radical, a $-(CH_2)_2R'_F$ group or a $-QNR_2$ group, $R^2$ denotes a hydrogen atom, an alkyl radical as defined for $R^1$ or, provided that $R^1$ is an alkyl or allyl radical, an allyl radical, $R^3$ denotes an alkyl or aralkyl radical as defined for $R^1$, an allyl, methallyl or propargyl radical or a $-CH_2-S-(CH_2)_2-R'_F$ group and $Z^{(-)}$ denotes a monovalent anion or its equivalent.

As substituents which may be present on the alkyl, aryl or aralkyl radicals there may be mentioned halogen atoms, hydroxyl, mercapto and nitrile groups and ester, acid, sulphonate, sulphate or carboxylate functional groups.

The compounds according to the invention in which X is the $-N=C=S$ group, that is polyfluoroalkyl isothiocyanates of formula:

$$R_F-(CH_2)_2-N=C=S \quad (I)$$

can be prepared, in comparable yields, from the corresponding polyfluoroalkyl azides $R_F(CH_2)_2N_3$ or polyfluoroalkylamines $R_F-(CH_2)_2-NH_2$.

The process for preparing isothiocyanates (I) from polyfluoroalkyl azides is carried out in a single reactor and comprises two stages:

1) The first consists in forming an iminophosphorane intermediate which is not isolated, by reacting the azide $R_F(CH_2)_2N_3$ under inert atmosphere with a triarylphosphine whose aryl radicals may be substituted by halogen atoms or lower alkyl or alkoxy groups, or else with a trialkyl phosphite whose alky radicals may contain from 1 to 4 carbon atoms. This reaction is advantageously carried out at a temperature of between 10° and 40° C. and, optionally, in the presence of an anhydrous aprotic organic solvent such as an ether, a halogenated or aromatic hydrocarbon or acetonitrile.

2) The second stage consists in reacting the iminotriarylphosphorane or iminotrialkoxyphosphorane intermediate, without preliminary isolation, with carbon sulphide. The addition of the latter is advantageously performed at a temperature of between 0° and 40° C. The reaction time varies from approximately 2 to 24 hours depending on the phosphorous intermediate used.

The preparation of isothiocyaates (I) from polyfluoroalkylamines is also carried out in a single reactor and comprises two stages:

1) The first consists in forming a polyfluoroalkyl dithiocarbamate by reacting the polyfluoroalkylamine $R_F(CH_2)_2NH_2$, in the presence of one molar equivalent of an inorganic or organic base, with carbon sulphide, the latter being preferably used in slight excess (0.2 to 0.5%). This reaction is advantageously carried out between −10° and +30° C. for a period of approximately 2 to 5 hours, and is then optionally taken to completion by heating to 90°–100° C. Water is a suitable solvent, but it is also possible to use methanol or an aqueous solution containing 50-60% of tert-butanol. The base preferably used is sodium or potassium hydroxide, but another base, for example aqueous ammonia or triethylamine, may be used; with the latter, dioxane or benzene can be used as a solvent.

2) The second stage consists in subjecting the polyfluoroalkyl dithiocarbamate to a carboalkoxylation or an oxidation. The carboalkoxylation is carried out by slow addition of one molar equivalent of a lower alkyl ($C_1$–$C_4$) chloroformate at a temperature of between −10° and 40° C. A polyfluoroalkyl carboalkoxydithiocarbamate is formed, which decomposes to a polyfluoroalkyl isothiocyanate according to the invention.

The oxidation of the dithiocarbamate intermediate can be carried out by reaction with an alkali metal hypochlorite between 0° and 8° C. in the presence of a chlorinated solvent (for example chloroform, methylene chloride or carbon tetrachloride) for 0.5 to 3 hours. This method gives a yield of polyfluoroalkyl isothiocyanate of the same order as the carboalkoxylation method.

The isothiocyanates (I) are valuable intermediates for the synthesis of precursors of surface-active agents, especially for that of polyfluorocarbodiimides and thioureas.

Thus, for example, the compounds according to the invention, in which X is an $-N=C=N(CH_2)_2-R'_F$ group, that is N,N'-bis(polyfluoroalkyl)carbodiimides of formula:

$$R_F(CH_2)_2-N=C-N(CH_2)_2R'_F \quad (II)$$

can be prepared by reacting an isothiocyanate (I) with an iminotriarylphosphorane obtained as above from a polyfluoroalkyl azide. The process is carried out in a single reactor where, in a first stage, the polyfluoroalkyl azide is converted into an iminotriarylphosphorane intermediate, which is not isolated but is reacted directly with the isothiocyanate (I) at a temperature of between 60° and 90° C. for a period of approximately 6 to 24 hours. This process enables symmetrical as well as unsymmetrical carbodiimides (II) to be obtained.

The symmetrical carbodiimides:

$$R_F(CH_2)_2-N=C=N-(CH_2)_2R_F \quad (IIa)$$

can also be obtained by another method from an azide $R_F(CH_2)_2N_3$ and carbon dioxide gas. By operating as above, the azide is first converted into an iminotriarylphosphorane intermediate and then, without preliminary isolation and in the same reactor, this intermediate is reacted with carbon dioxide gas.

The carbodiimides (II) according to the invention are valuable intermediates for the synthesis of precursors of surface-active agents and of fluoroureas. They can also be used as stabilizers for natural or synthetic polymers, increasing their resistance to hydrolysis. In addition, they can be used for producing neutral lubricating oils or, yet again, as monomers which lead to highly hydrophobic plastics.

The compounds according to the invention in which X is a thiourea group $-NH-CS-A$, that is the compounds of formula:

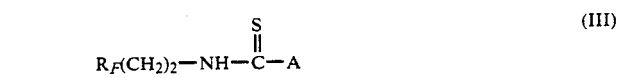

are prepared from the isothiocyanates of formula (I).

Thus, the monosubstituted thioureas of formula:

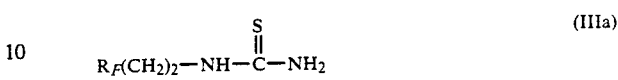

can be obtained by reaction of aqueous ammonia with an isothiocyanate (I). This reaction is advantageously carried out at a temperature of between 20° and 80° C. by using an aqueous solution containing 28–30% of $NH_4OH$ in a proportion of three moles of aqueous ammonia per mole of isothiocyanate. In these conditions, a monosubstituted thiourea (IIIa) is obtained, sufficiently pure to be usable directly.

The di- or trisubstituted thioureas of formula:

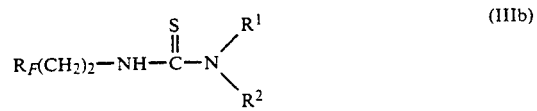

are obtained by reacting the corresponding primary or secondary amine $HNR^1R^2$ with an isothiocyanate (I). The reaction is preferably carried out at a temperature of between 0° and 40° C., optionally in an inert organic solvent such as, for example, an ether, a halogenated hydrocarbon or acetonitrile.

Among the thioureas (IIIb), those in which $R^1$ denotes a dialkylaminoalkyl group and $R^2$ denotes a hydrogen atom, that is the compounds of formula:

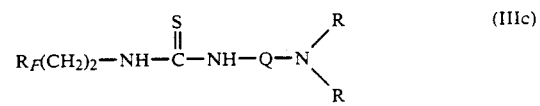

have a tertiary amine functional group which makes them reactive towards quaternizing agents. Thus, the compounds of formula (III) in which A denotes a nitrogen group (A3), that is the ammonium salts of formula:

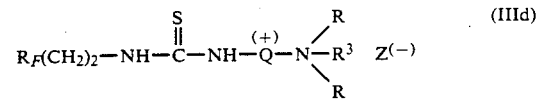

can be prepared by reaction of a thiourea (IIIc) with a quaternizing agent, for example an optionally functionalized alkyl halide. The reaction is preferably carried out by dissolving substantially equimolar quantities of thiourea (IIIc) and of the chosen quaternizing agent in an inert anhydrous organic solvent (for example an ether, a halogenated hydrocarbon or acetonitrile) at a temperature of between 20° and 80° C. The reaction time and the physical appearance of the salts (IIId) which are formed vary depending on the nature of the chosen quaternizing agent. However, most of the salts (IIId) are colorless pastes or oils and are hygroscopic; to a different extent, they are all soluble in water and form neutral solutions.

Nonlimiting examples of quaternizing agents which may be mentioned more particularly are alkyl iodides (1 to 18 carbon atoms), allyl bromide, hydroxyethyl bromide, benzyl bromide, alkyl bromides (4 to 18 carbon atoms) and polyfluoroalkylthiomethyl bromides $R'_F(CH_2)_2—S—CH_2Br$, described in French patent no. 2,592,648.

Provided that a double molar proportion of thiourea (IIIc) is used, it is also possible to use as quaternizing agents alkyl dihalides such as, for example, 1,2-dibromoethane, 1,3-dibromopropane, 1,2-diiodoethane, 1,3-diiodopropane and 1,4-diiodobutane. Compounds of formula (III) are then obtained, in which A denotes the group (A4), that is the double salts of formula:

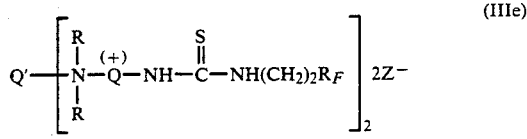

The anion $Z^{(-)}$ of the ammonium salts (IIId) and (IIIe) can, if desired, be easily exchanged for another anion using methods which are known per se. More specific examples of anions which may be mentioned are halide, nitrate, p-toluenesulphonate, sulphate, alkylsulphate and picrate ions.

The compounds of formula (III) in which A denotes a group (A5), namely the N-oxides of formula:

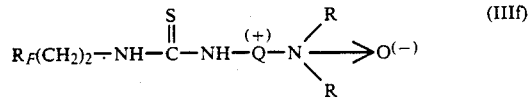

can be prepared by reaction of hydrogen peroxide with a thiourea (IIIc) in an inert solvent (for example an ether or acetonitrile) at a temperature of between 60° and 80° C. These oxides are obtained in the form of pastes and are all water-soluble.

The compounds of formula (III) for which A denotes the group (A6), that is the betaines of formula:

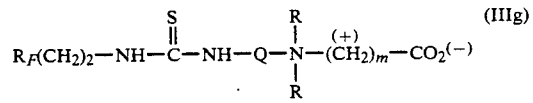

can be prepared by the action of sodium chloroacetate or of beta-propiolactone on a thiourea (IIIc). The reaction is advantageously carried out at a temperature of between 30° and 90° C. in an inert organic solvent (for example an alcohol or trichlorotrifluoroethane). The betaines (IIIg) are obtained in the form of pastes; they are all water-soluble.

The ammonium salts (IIId) and (IIIe), the N-oxides (IIIf) and the betaines (IIIg) are valuable surface-active agents which can be employed as additives in a very wide variety of fields as wetting agents, emulsifiers, dispersants or foaming agents.

EXAMPLES

The following examples illustrate the invention without limiting it.

EXAMPLE 1

0.02 moles of 2-perfluorobutylethyl azide $C_4F_9—C_2H_4—N_3$ are introduced into a reactor placed under nitrogen atmosphere and equipped with a magnetic stirrer and a dropping funnel containing 0.02 moles of triphenylphosphine in solution in 26 ml of anhydrous tetrahydrofuran, and the triphenyl phosphine solution is then added dropwise at room temperature.

After being stirred for one hour at room temperature, the solution is cooled to 0° C. by means of an ice bath, and 15 g of carbon sulphide are then added dropwise. When the addition is finished the ice bath is removed and stirring is continued for two hours.

The tetrahydrofuran and the excess carbon sulphide are then evaporated off under vacuum and the residue is then taken up with petroleum ether and filtered. After evaporation of the solvent under vacuum 2-perfluorobutylethyl isothiocyanate $C_4F_9—C_2H_4—NCS$, which boils at 48° C. at 4 kPa, is obtained in a 69% yield.

This isothiocyanate was identified by the following data:

| | Elemental analysis: | | | | |
|---|---|---|---|---|---|
| | C % | H % | F % | N % | S % |
| measured | 27.61 | 1.33 | 56.00 | 4.54 | 10.49 |
| calculated | 27.54 | 1.31 | 56.06 | 4.59 | 10.50 |

Infrared spectrum
$v_{(C-F)} = 1050-1350$ cm$^{-1}$
$v_{(NCS)} = 2075$ cm$^{-1}$ shoulder at 2190 cm$^{-1}$ $^1$H NMR spectrum recorded in solution in CDCl$_3$, the chemical shifts being given in ppm relative to TMS:
split triplet at 2.51 ppm (2H integration, $^3J_{H-F} = 13.5$ Hz and $^3J_{H-H} = 5.6$ Hz)
triplet at 3.86 ppm (2H integration, $^3J_{H-H} = 5.6$ Hz)

$^{19}$F NMR spectrum recorded in solution in CDCl$_3$, the chemical shifts being given in ppm relative to CFCl$_3$:

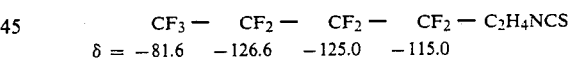

Mass spectrometry
M$^+$ = 305 (29%); m/z 156 (22%); m/z 126 (16%); m/z 110 (21%); m/z 93 (63.5%); m/z 72 (100%); m/z 69 (20.5%).

EXAMPLE 2

The procedure is as in Example 1, but replacing 2-perfluorobutylethyl azide with the same molar quantity of 2-perfluorohexylethyl azide. The corresponding isothiocyanate $C_6F_{13}—C_2H_4—NCS$ is obtained in a 70% yield (B.p. = 87°-91° C./2.67 kPa).

This isothiocyanate was identified by the following data:

| | Elemental analysis: | | | | |
|---|---|---|---|---|---|
| | C % | H % | F % | N % | S % |
| measured | 26.55 | 1.11 | 60.97 | 3.50 | 7.86 |
| calculated | 26.67 | 0.99 | 60.98 | 3.45 | 7.90 |

$^{19}$F NMR spectrum

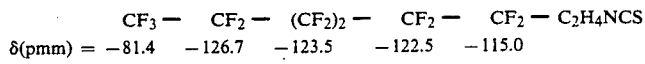

Mass spectrometry $M^+ = 405$ (87%); m/z 386 (2.5%); m/z 136 (2%); m/z 131 (15%); m/z 119 (22%); m/z 108 (11.5%); m/z 72 (99%); m/z 59 (100%).

IR and $^1H$ NMR spectra: identical with those of the isothiocyanate of Example 1.

EXAMPLE 3

The procedure is as in Example 1, but replacing 2-perfluorobutylethyl azide with the same molar quantity of 2-perfluorooctylethyl azide. The corresponding isothiocyanate $C_8F_{17}$—$C_2H_4$—NCS is obtained in a 73% yield (B.p.=113°-15° C./4 kPa).

This isothiocyanate has the following characteristics:

| | Elemental analysis: | | | | |
|---|---|---|---|---|---|
| | C % | H % | F % | N % | S % |
| measured | 26.30 | 0.78 | 63.85 | 2.72 | 6.34 |
| calculated | 26.13 | 0.79 | 63.96 | 2.77 | 6.33 |

IR and $^1H$ NMR spectra: identical with those of the isothiocyanate of Example 1.

$^{19}F$ NMR spectrum

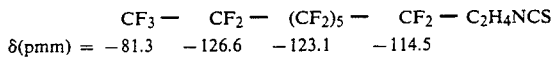

Mass spectrometry $M^+ = 505$ (46.5%); m/z 119 (15%); m/z 72 (100%); m/z 69 (34.5%); m/z 59 (57%).

EXAMPLE 4

0.02 moles of 2-perfluorohexylethyl azide are introduced into a reactor placed under a nitrogen atmosphere and equipped with a magnetic stirrer and a dropping funnel containing 0.02 moles of trimethyl phosphite in solution in 26 ml of anhydrous tetrahydrofuran, and the trimethyl phosphite solution is then added at room temperature.

After 20 hours' stirring, 15 g of carbon sulphide are added dropwise at room temperature. Stirring is then continued for 24 hours and the tetrahydrofuran and excess carbon sulphide are then evaporated off under reduced pressure, and the residue is distilled. 2-Perfluorohexylethyl isothiocyanate is thus obtained in a 55% yield (B.p.=87°-91° C./2.67 kPa).

EXAMPLE 5

0.66 g of caustic soda in 3.6 ml of water and 1.258 g of carbon sulphide are placed in a reactor equipped with a magnetic stirrer, a condenser and a dropping funnel. 0.0165 moles of 2-perfluorobutylethylamine $C_4F_9$—$C_2H_4$—$NH_2$ are added very slowly. The reaction mixture turns orange and becomes pasty. 2.5 to 3 ml of water are added and stirring is continued for two hours at room temperature, and then for 15 minutes at 90° C. The mixture is then cooled to 40° C. and 0.0165 moles of methyl chloroformate are added slowly. Stirring is continued for one hour at room temperature, followed by extraction with ether, drying over sodium sulphate and evaporation. When the residue is distilled, 2-perfluorobutylethyl isothiocyanate is obtained in a 65% yield (B.p.=48° C./4kPa).

EXAMPLE 6

The procedure is as in Example 5, but replacing 2-perfluorobutylethylamine with the same molar quantity of 2-perfluorohexylethylamine. 2-Perfluorohexylethyl isothiocyanate is obtained in a 76% yield (B.p.=90° C./2.67 kPa).

EXAMPLE 7

The procedure is as in Example 5, but replacing 2-perfluorobutylethylamine with the same molar quantity of 2-perfluorooctylethylamine. 2-Perfluorooctylethyl isothiocyanate is obtained in a 67% yield (B.p.=113°-15° C./4 kPa).

EXAMPLE 8

0.66 g of caustic soda in 3.6 ml of water and 1.258 g of carbon sulphide are placed in a reactor equipped with a magnetic stirrer, a condenser and a dropping funnel. 0.0165 moles of 2-perfluorobutylethylamine are added very slowly via the dropping funnel. The reaction mixture turns orange and becomes pasty. 2.5 to 3 ml of water are then added and stirring is continued for two hours at room temperature and then for 15 minutes at 90° C. The mixture is then cooled to 0° C. and 16 ml of water and 10 ml of methylene chloride are added, following by a solution of 33 ml of sodium hypochlorite at a strength of 10-13 French chlorometry degrees (d=1.05), to which 2.65 g of caustic soda have been added. The mixture changes from yellow to milky white. When the addition is finished, stirring is continued for one hour and an extraction with ether is then carried out, followed by drying over sodium sulphate and evaporation. When the residue is distilled, 2-perfluorobutylethyl isothiocyanate is obtained in a 62% yield (B.p.=48° C./4 kPa).

EXAMPLE 9

The procedure is as in Example 8, but replacing 2-perfluorobutylethylamine with the same molar quantity of 2-perfluorohexylethylamine. The corresponding isothiocyanate is obtained in a 65% yield (B.p.=90° C./2.67 kPa).

EXAMPLE 10

The procedure is as in Example 8, but replacing 2-perfluorobutylethylamine with the same molar quantity of 2-perfluorooctylethylamine. The corresponding isothiocyanate is obtained in a 70% yield (B.p.=113°-15° C./4 kPa; mp=50° C.).

EXAMPLE 11

0.02 moles of 2-perfluorohexylethyl azide are introduced into a reactor placed under a nitrogen atmosphere and equipped with a magnetic stirrer and a dropping funnel containing 0.02 moles of triphenylphosphine in solution in 26 ml of anhydrous tetrahydrofuran and the triphenyl phosphine solution is then added dropwise at room temperature.

After one hour's stirring, carbon dioxide gas obtained by sublimation of carbon dioxide snow and predried over anhydrous $CaCl_2$ is bubbled into the reaction mixture.

After one hour's reaction, the solvent is evaporated off and the residue is taken up with petroleum ether. This is filtered to remove the solid triphenylphosphine oxide and the petroleum ether is then evaporated off under vacuum and the residue is distilled under nitrogen atmosphere.

N,N'-bis(2-perfluorohexylethyl)carbodiimide: $C_6F_{13}$—$C_2H_4$—N=C=N—$C_2H_4$—$C_6F_{13}$ is thus obtained in a 70% yield (B.p.=101° C./4 kPa).

If white solid particles are present in the product after distillation, the carbodiimide must be filtered to remove this small quantity of urea formed during the distillation.

EXAMPLE 12

The procedure is as in Example 11, but replacing 2-perfluorohexylethyl azide with the same molar quantity of 2-perfluorobutylethyl azide. The corresponding carbodiimide $C_4F_9$—$C_2H_4$—N=C=N—$C_2H_4$—$C_4F_9$, is obtained in a 68% yield (B.p.=67°-70° C./133 Pa, distillation under $N_2$).

EXAMPLE 13

The procedure as in Example 11, but replacing 2-perfluorohexylethyl azide with the same molar quantity of 2-perfluorooctylethyl azide and petroleum ether with 1,1,2-trichloro-1,2,2-trifluoroethane. The corresponding carbodimide $C_8F_{17}$—$C_2H_4$—N=C=N—$C_2H_4$—$C_8F_{17}$ is obtained in a 65% yield (bulb tube distillation, oven temperature: 120° C./10 Pa).

EXAMPLE 14

0.01 mole of 2-perfluorohexylethyl azide is introduced into a reactor placed under nitrogen atmosphere and equipped with a magnetic stirrer and a dropping funnel containing 0.01 mole of triphenylphosphine in solution in 13 ml of anhydrous tetrahydrofuran. The triphenylphosphine solution is then added dropwise at room temperature.

After one hour's stirring, a solution of 0.01 mole of 2-perfluorohexylethyl isothiocyanate in 13 ml of tetrahydrofuran is added via the dropping funnel.

If the reaction, which is followed by gas phase chromatography, is not finished after 12 hours' stirring at ambient temperature, heating to 70° C. is applied for a few hours.

The tetrahydrofuran is then evaporated off under vacuum and the residue is taken up with petroleum ether. The triphenylphosphine sulphide formed is filtered off and then the petroleum ether is stripped off under vacuum and the residue is distilled under nitrogen atmosphere.

N,N'-bis(2-perfluorohexylethyl)carbodiimide is thus obtained in a 78% yield (B.p.=101° C./4 kPa).

EXAMPLE 15

The procedure is as in Example 14, but replacing 2-perfluorohexylethyl azide with the same molar quantity of 2-perfluorobutylethyl azide and 2-perfluorohexylethyl isothiocyanate with the same molar quantity of 2-perfluorobutylethyl isothiocyanate.

N,N'-bis(perfluorobutylethyl)carbodiimide is obtained in a 75% yield (B.p.=67°-70° C./133 Pa, distillation under $N_2$).

EXAMPLE 16

The procedure as in Example 14, but replacing 2-perfluorohexylethyl azide with the same molar quantity of 2-perfluorobutylethyl azide.

N-(2-perfluorobutylethyl)-N'(2-perfluorohexylethyl) carbodiimide $C_4F_9$—$C_2H_4$—N=C=N—$C_2H_4$—$C_6F_{13}$ is obtained in a 60% yield (B.p.=97° C./4 kPa, distillation under $N_2$).

The carbodiimides of Examples 11 to 16 were identified by elemental analysis, infrared, proton and fluorine NMR and mass spectrometry. The data corresponding to the elemental analysis and to the mass spectrometry are collated in Table 1, which follows.

TABLE 1

| CARBODIIMIDE | $C(=NC_2H_4C_4F_9)_2$ | $C(=NC_2H_4C_6F_{13})_2$ | $C(=NC_2H_4C_8F_{17})_2$ | $C(NC_2H_4C_4F_9)(NC_2H_4C_6F_{13})$ |
|---|---|---|---|---|
| Elemental analysis | | | | |
| C % measured (calculated) | 29.28 (29.21) | 28.01 (27.79) | 27.24 (26.98) | 28.04 (28.39) |
| H % measured (calculated) | 1.68 ( 1.50) | 1.07 ( 1.09) | 1.14 ( 0.86) | 1.15 ( 1.26) |
| F % measured (calculated) | 64.00 (64.04) | 66.95 (67.30) | 69.17 (69.16) | 66.24 (65.93) |
| N % measured (calculated) | 5.11 ( 5.24) | 3.90 ( 3.81) | 2.43 ( 3.00) | 4.55 ( 4.42) |
| Mass spectrum | $M^+$. = 534 (10%) | $M^+$. = 734 (3%) | $M^+$. = 934 (8%) | $M^+$. = 634 (11.5%) |
| | m/z 515 (3%) | m/z 715 (4.5%) | m/z 915 (7.5%) | m/z 615 (8.5%) |
| | m/z 301 (100%) | m/z 401 (100%) | m/z 501 (100%) | m/z 401 (100%) |
| | m/z 119 (7%) | m/z 119 (4.5%) | m/z 169 (7%) | m/z 301 (99%) |
| | m/z 69 (12.5%) | m/z 69 (13%) | m/z 119 (5%) | m/z 119 (12%) |
| | m/z 55 (99%) | m/z 55 (82%) | m/z 69 (18%) | m/z 81 (11.5%) |
| | | | m/z 55 (90%) | m/z 69 (40%) |
| | | | | m/z 55 (99%) |

In the case of all the carbodiimides the IR spectra give:

$\nu_{C-F}$ = 1000–1300 cm$^{-1}$
$\nu_{N=C=N}$ = 2125 cm$^{-1}$

The $^1$H NMR spectra are identical with those of the isothiocyanates RFC2H4NCS (signals, integration, coupling constants).

In $^{19}$F NMR, the spectra of symmetrical carbodiimides (Examples 11 to 15) are identical with those of the corresponding isothiocyanates. In the case of the unsymmetrical carbodiimide of Example 16, the two terminal $CF_3$ groups show the same chemical shift and resonate at −81.5 ppm; the two $CF_2\alpha$ and the two $CF_2\omega$ also have the same chemical shift, at −115.0 and −126.7 ppm respectively; the other $CF_2$ groups give a system of four peaks between −125.1 and −122.0 ppm whose relative integration corresponds to eight fluorine atoms.

EXAMPLE 17

0.01 mole of 2-perfluorohexylethyl isothiocyanate is introduced at room temperature into a reactor equipped with a condenser and fitted with a magnetic stirrer and 6.6 g of a 28-30% solution of NH4OH are then added dropwise. The reaction mixture is then stirred for one hour at room temperature and the condenser is then removed and the mixture is heated at 70-80° C. for 2 hours in order to evaporate off the excess aqueous ammonia. The white solid formed is dried and N-(2-perfluorohexylethyl)thiourea $C_6F_{13}-C_2H_4-NH-C-S-NH_2$ which melts at 126° C. and has the following analytical characteristics is thus obtained in an 89% yield:

|  | Elemental analysis: | | | | |
| --- | --- | --- | --- | --- | --- |
|  | C % | H % | F % | N % | S % |
| measured | 25.83 | 1.52 | 58.74 | 6.64 | 7.50 |
| calculated | 25.60 | 1.66 | 58.63 | 6.63 | 7.58 |

IR spectrum
$\nu_{C-F} = 1100-1300$ cm$^{-1}$
$\nu_{NH2} = 3400$ cm$^{-1}$
$\nu_{NH} = 3290$ cm$^{-1}$
$\nu_{C=S} = 1580$ cm$^{-1}$ $^1$H NMR spectrum recorded in acetone-d$_6$, the chemical shifts being given in ppm relative to TMS:
broadened singlet at 7.37 ppm (1H integration)
ill-resolved signal at 6.75 ppm (2H integration)
multiplet at 2.62 ppm (split triplet - 2H integration, $^3J_{H-F} = 13.5$ Hz; $^3J_{H-H} = 7.5$ Hz)
quadruplet at 3.87 ppm (2H integration, $^3J_{H-H} = 6.5$ Hz through the nitrogen atom).

$^{19}$F NMR spectrum recorded in acetone-d$_6$, the chemical shifts being given relative to CFCl$_3$:

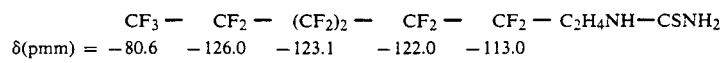

| CF$_3$ — | CF$_2$ — | (CF$_2$)$_2$ — | CF$_2$ — | CF$_2$ — | C$_2$H$_4$NH—CSNH$_2$ |
| --- | --- | --- | --- | --- | --- |
| $\delta$(pmm) = −80.6 | −126.0 | −123.1 | −122.0 | −113.0 | |

Mass spectrometry
M$^+$ = 422 (42%); m/z 389 (4%); m/z 362 (12%); m/z 153 (5.5%) m/z 103 (25%); m/z 69 (33.5%); m/z 55 (100%).

By following the same procedure with 2perfluorobutylethyl isothiocyanate, N-(2-perfluorobutylethyl) thiourea, which melts at 113° C. and has the following characteristics, is obtained in a 90% yield:

|  | Elemental analysis: | | | | |
| --- | --- | --- | --- | --- | --- |
|  | C % | H % | F % | N % | S % |
| measured | 25.88 | 2.03 | 53.25 | 8.85 | 10.00 |
| calculated | 26.08 | 2.17 | 53.10 | 8.70 | 9.94 |

IR and $^1$H spectra identical with those of the preceding compound.

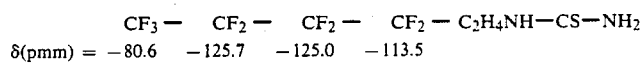

| CF$_3$ — | CF$_2$ — | CF$_2$ — | CF$_2$ — | C$_2$H$_4$NH—CS—NH$_2$ |
| --- | --- | --- | --- | --- |
| $\delta$(pmm) = −80.6 | −125.7 | −125.0 | −113.5 | |

Mass spectrometry
M$^+$ = 322 (49%); m/z 289 (11%); m/z 201 (11.5%); m/z 103 (15.5%) m/z 77 (23%); m/z 69 (68%); m/z 60 (62%); m/z 55 (100%).

EXAMPLE 18

The N,N'-disubstituted and N,N',N'-trisubstituted thioureas of formula:

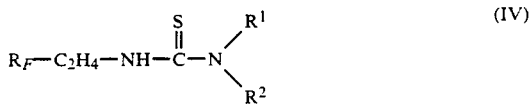

$$R_F-C_2H_4-NH-\underset{\underset{S}{\|}}{C}-N\overset{R^1}{\underset{R^2}{\diagdown}} \quad (IV)$$

are prepared from the amines NHR$^1$R$^2$ by proceeding as follows:

0.01 mole of the amine NHR$^1$R$^2$ in solution in 15 ml of ethyl ether (or of ethanol in the case where the amine used is diethanolamine) is introduced into a round bottom reactor fitted with a magnetic stirrer and a dropping funnel containing 0.01 mole of 2-perfluoroalkylethyl isothiocyanate R$_F$C$_2$H$_4$NCS previously dissolved in 15 ml of ethyl ether, and the isothiocyanate R$_F$C$_2$H$_4$NCS solution is then added with stirring at room temperature. The reaction is practically immediate.

Stirring is nevertheless continued until all the isothiocyanate is consumed. Depending on the nature of the starting amine, the product either precipitates in the reaction medium or does not do so. In all cases it suffices to strip off the solvent in the rotary evaporator and to wash the residue thus obtained abundantly with petroleum ether.

The thioureas of formula (IV) are thus obtained in most cases in the form of a white solid, sometimes in the form of a translucent oil. Their melting points and the reaction yields are shown in the sixth and fifth columns of Table 2, which follows, the number Tx of the first column being used to identify each product.

The results obtained from the elemental analysis and mass spectrometry are collated in Tables 3 and 4.

TABLE 2

| THIOUREAS OF FORMULA (IV) | | | | | |
| --- | --- | --- | --- | --- | --- |
| No. | R$_F$ | R$^1$ | R$^2$ | Yld (%) | Mp (°C.) |
| T1 | C$_4$F$_9$ | CH$_2$—CH=CH$_2$ | H | 77 | (oil) |
| T2 | C$_6$F$_{13}$ | CH$_2$—CH=CH$_2$ | H | 88 | 30 |
| T3 | C$_8$F$_{17}$ | CH$_2$—CH=CH$_2$ | H | 83 | 80-82 |
| T4 | C$_4$F$_9$ | CH$_2$—CH=CH$_2$ | CH$_2$—CH=CH$_2$ | 95 | (oil) |
| T5 | C$_6$F$_{13}$ | CH$_2$—CH=CH$_2$ | CH$_2$—CH=CH$_2$ | 70 | (oil) |
| T6 | C$_8$F$_{17}$ | CH$_2$—CH=CH$_2$ | CH$_2$—CH=CH$_2$ | 78 | 30 |

TABLE 2-continued
THIOUREAS OF FORMULA (IV)

| No. | $R_F$ | $R^1$ | $R^2$ | Yld (%) | Mp (°C.) |
|---|---|---|---|---|---|
| T7 | $C_4F_9$ | $C_2H_4N(CH_3)_2$ | H | 77 | 62 |
| T8 | $C_6F_{13}$ | $C_2H_4N(CH_3)_2$ | H | 92 | 63 |
| T9 | $C_8F_{17}$ | $C_2H_4N(CH_3)_2$ | H | 87 | 80 |
| T10 | $C_4F_9$ | $C_3H_6N(CH_3)_2$ | H | 83 | 36 |
| T11 | $C_6F_{13}$ | $C_3H_6N(CH_3)_2$ | H | 85 | 52–53 |
| T12 | $C_8F_{17}$ | $C_3H_6N(CH_3)_2$ | H | 87 | 71–73 |
| T13 | $C_4F_9$ | $C_2H_4OH$ | $C_2H_4OH$ | 93 | (oil) |
| T14 | $C_6F_{13}$ | $C_2H_4OH$ | $C_2H_4OH$ | 96 | (oil) |
| T15 | $C_6F_{13}$ | phenyl | H | 82 | 93 |
| T16 | $C_8F_{17}$ | phenyl | H | 80 | 117 |
| T17 | $C_4F_9$ | $C_4H_9$ | H | 89 | 56 |
| T18 | $C_6F_{13}$ | $C_4H_9$ | H | 71 | 67 |
| T19 | $C_6F_{13}$ | $C_8H_{17}$ | H | 84 | 73 |
| T20 | $C_8F_{17}$ | $C_8H_{17}$ | H | 91 | 85 |
| T21 | $C_4F_9$ | $C_2H_4C_4F_9$ | H | 70 | 67 |
| T22 | $C_6F_{13}$ | $C_2H_4C_4F_9$ | H | 82 | 73 |
| T23 | $C_6F_{13}$ | $C_2H_4C_6F_{13}$ | H | 87 | 88 |
| T24 | $C_8F_{17}$ | $C_2H_4C_4F_9$ | H | 80 | 86–87 |

TABLE 3
Percentage analysis of thioureas T1 to T24

| THIOUREA No. | C % | H % | F % | N % | S % |
|---|---|---|---|---|---|
| T1 | 32.42 | 3.09 | 47.06 | 7.78 | 8.66 |
| T2 | 31.29 | 2.45 | 53.01 | 6.12 | 7.12 |
| T3 | 26.95 | 2.12 | 57.74 | 4.70 | 5.49 |
| T4 | 39.02 | 3.75 | 42.88 | 6.93 | 7.43 |
| T5 | 36.05 | 3.12 | 49.02 | 5.63 | 6.17 |
| T6 | 33.69 | 2.44 | 53.66 | 4.29 | 5.90 |
| T7 | 33.72 | 4.27 | 43.24 | 10.55 | 8.22 |
| T8 | 31.67 | 3.12 | 50.00 | 8.55 | 6.64 |
| T9 | 30.10 | 2.85 | 54.55 | 7.06 | 5.45 |
| T10 | 35.21 | 4.43 | 41.85 | 10.61 | 7.89 |
| T11 | 33.43 | 3.27 | 48.75 | 8.23 | 6.32 |
| T12 | 31.60 | 3.21 | 53.25 | 6.68 | 5.26 |
| T13 | 32.30 | 3.82 | 41.75 | 6.73 | 7.77 |
| T14 | 30.73 | 2.90 | 48.30 | 5.52 | 6.26 |
| T15 | 36.27 | 2.13 | 49.73 | 5.83 | 6.05 |
| T16 | 34.27 | 1.89 | 53.87 | 4.57 | 5.39 |
| T17 | 34.78 | 4.09 | 45.25 | 7.38 | 8.48 |
| T18 | 32.89 | 3.25 | 51.05 | 5.78 | 7.02 |
| T19 | 38.25 | 4.30 | 46.38 | 5.37 | 5.70 |
| T20 | 35.75 | 3.58 | 51.15 | 4.40 | 5.10 |
| T21 | 27.73 | 1.89 | 60.10 | 4.79 | 5.50 |
| T22 | 26.81 | 1.65 | 62.87 | 4.33 | 4.34 |
| T23 | 26.81 | 1.45 | 64.55 | 3.68 | 3.91 |
| T24 | 26.43 | 1.38 | 64.40 | 3.70 | 4.08 |

TABLE 4

| THIOUREA No. | MASS SPECTRUM |
|---|---|
| T1 | $M^+ \cdot 362$ (15%), m/z 347 (30%), m/z 72 (100%), m/z 69 (57.5%) |
| T2 | $M^+ \cdot 462$ (18.5%), m/z 447 (35%), m/z 405 (16%), m/z 72 (100%), m/z 69 (50.5%), m/z 57 (88.5%) |
| T3 | $M^+ \cdot 562$ (21%), m/z 72 (100%), m/z 69 (50%), m/z 57 (91.5%) |
| T4 | $M^+ \cdot 402$ (23%), m/z 56 (100%), m/z 41 (87%), m/z 69 (43%), |
| T5 | $M^+ \cdot 502$ (12%), m/z 56 (100%), m/z 41 (90%), |
| T6 | $M^+ \cdot 602$ (28%), m/z 56 (100%), m/z 41 (84%), m/z 77 (23%), m/z 69 (33%) |
| T7 | $M^+ \cdot 393$ (6%), m/z 72 (96.5%), m/z 71 (100%), m/z 69 (49%) |
| T8 | $M^+ \cdot 493$ (6%), m/z 71 (77.5%), m/z 58 (100%) |
| T9 | $M^+ \cdot 593$ (6.5%), m/z 71 (75%), m/z 72 (97%), m/z 58 (100%) |
| T10 | $M^+ \cdot 407$ (10%), m/z 72 (10%), m/z 86 (14%), m/z 58 (100%) |
| T11 | $M^+ \cdot 507$ (9%), m/z 72 (13%), m/z 58 (100%) |
| T12 | $M^+ \cdot 607$ (10%), m/z 72 (15.5%), m/z 58 (100%) |
| T13 | $(M + 1)^+ 411$ (3%), $M^+ \cdot 410$ (2%), m/z 74 (81%) m/z 43 (100%), m/z 69 (47.5%) |
| T14 | $(M + 1)^+ 511$ (3%), $M^+ \cdot 510$ (1.5%), m/z 74 (81%) m/z 57 (60%), m/z 43 (100%), m/z 69 (49%) |
| T15 | $M^+ \cdot 498$ (45%), m/z 465 (18.5%), m/z 93 (100%), m/z 77 (76.5%), m/z 69 (46%) |
| T16 | $M^+ \cdot 598$ (40%), m/z 565 (21.5%), m/z 93 (100%), m/z 77 (79.5%), m/z 69 (47.5) |
| T17 | $M^+ \cdot 398$ (20%), m/z 72 (75%), m/z 44 (100%) |
| T18 | $M^+ \cdot 478$ (21%), m/z 72 (71%), m/z 44 (100%) |
| T19 | $M^+ \cdot 526$ (24%), m/z 72 (73%), m/z 44 (100%) |
| T20 | $M^+ \cdot 626$ (21.5%), m/z 72 (47%), m/z 69 (27.5%), m/z 44 (100%) |
| T21 | $M^+ \cdot 568$ (27.5%), m/z 119 (10%), m/z 69 (20%), m/z 44 (100%) |
| T22 | $M^+ \cdot 668$ (20%), m/z 119 (11.5%), m/z 69 (20%), m/z 44 (100%) |
| T23 | $M^+ \cdot 768$ (20%), m/z 119 (8%), m/z 69 (20%), m/z 44 (100%) |
| T24 | $M^+ \cdot 768$ (26%), m/z 119 (11%), m/z 69 (24.5%), m/z 44 (100%) |

The IR spectra of all the thioureas were recorded as a KBr disc, with the exception of the five oily products T1, T4, T5, T13, T14), in the case of which the spectra were produced in solution in $CHCl_3$. For a given single series, the spectrum is independent of the radical $R_F$:

| Thioureas T1 to T3: | $\nu C-F = 1100-1350$ cm$^{-1}$ |
|---|---|
| | $\nu C=S = 1580$ cm$^{-1}$ |
| | $\nu N-H = 3300$ cm$^{-1}$ |
| | $\nu C-H = 700-900$ cm$^{-1}$ |
| | $\nu C=C = 1653$ cm$^{-1}$ |
| Thioureas T4 to T6: | $\nu C-F = 1100-1350$ cm$^{-1}$ |
| | $\nu C=S = 1530$ cm$^{-1}$ |
| | $\nu N-H = 3320$ cm$^{-1}$ |
| | $\nu C=C = 1650$ cm$^{-1}$ |
| Thioureas T7 to T12: | $\nu C-F = 1100-1350$ cm$^{-1}$ |
| | $\nu C=S = 1580$ cm$^{-1}$ |
| | $\nu N-H = 3300, 3380$ cm$^{-1}$ |
| | $\nu C-H = 680-900$ cm$^{-1}$ |
| Thioureas T13 and T14: | $\nu C-F = 1100-1300$ cm$^{-1}$ |
| | $\nu C=S = 1585$ cm$^{-1}$ |
| | $\nu N-H = 3200$ cm$^{-1}$ |
| | $\nu O-H = 3320$ cm$^{-1}$ |
| Thioureas T15 and T16: | $\nu C-F = 1050-1350$ cm$^{-1}$ |
| | $\nu N-H = 3209, 3377$ cm$^{-1}$ |
| | $\nu C-S = 1555$ cm$^{-1}$ |
| | $\nu C-H = 650, 694, 737$ cm$^{-1}$ |
| Thioureas T17 to T20: | $\nu C-F = 1000-1350$ cm$^{-1}$ |
| | $\nu N-H = 3280$ cm$^{-1}$ |
| | $\nu C=S = 1570$ cm$^{-1}$ |
| | $\nu C-H = 850, 890$ cm$^{-1}$ |
| Thioureas T21 to T24: | $\nu C-F = 1000-1350$ cm$^{-1}$ |
| | $\nu N-H = 3380$ cm$^{-1}$ |

-continued $$\nu_{C=S} = 1637 \text{ cm}^{-1}$$

The $^1$H NMR spectra of thioureas T1 to T24 were recorded in acetone-d$_6$. All of them show a split triplet of 2H integration at 2.60 ppm ($^3J_{H\text{-}F}=19.5$ Hz; $^3J_{H\text{-}H3}=6.5$ Hz) and a quadruplet, also of 2H integration, at 3.90 ppm ($^3J_{H\text{-}H}=6.5$ Hz - coupling through the nitrogen atom); these two signals correspond to the CH$_2$ bonded to the R$_F$ radical and to the CH$_2$ bonded to the NH group respectively. In the case of each series, the nature of the radical R$_F$ does not effect the spectra, the other signals observed being the following:

| | |
|---|---|
| Thioureas T1 to T3: | broadened signal at 7.1 ppm (2H integ.) |
| | triplet at 4.17 ppm |
| | ($^3J = 6.5$ Hz - 2H integ.) |
| | multiplet between 4.91 and 5.35 ppm (2H) |
| | multiplet between 5.62 and 6.17 ppm (1H) |
| Thioureas T4 to T6: | signal at 6.94 ppm (1H integ.) |
| | doublet at 4.31 ppm (4H integ. - $^3J = 6.5$ Hz) |
| | multiplet between 4.91 and 5.35 ppm (4H) |
| | multiplet between 5.62 and 6.17 ppm (2H) |
| Thioureas T7 to T9: | quadruplet at 3.51 ppm (2H integ.) |
| | signal at 7.79 ppm (integ. 1H) |
| | signal at 6.98 ppm (integ. 1H) |
| | singlet at 2.34 ppm (6H integ.) |
| | multiplet between 2.31 and 2.98 ppm (4H integ.) |
| Thioureas T10 to T12: | quadruplet at 3.48 ppm (2H integ.) |
| | signal at 7.59 ppm (1H integ.) |
| | signal at 7.96 ppm (1H integ.) |
| | singlet at 2.19 ppm (6H integ.) |
| | triplet at 2.34 ppm (2H integ.) |
| | quintuplet at 1.71 ppm (2H integ.) |
| Thioureas T13 and T14: | multiplet at 4.00 ppm 12H integ.) |
| Thioureas T15 and T16: | signal at 8.98 ppm (1H integ.) |
| | multiplet at 7.25 ppm (6H integ.) |
| Thioureas T17 to T20: | signal at 6.98 ppm (2H integ.) |
| | quadruplet at 3.47 ppm (2H integ. - $^3J = 6.5$ Hz) |
| | multiplet between 1.13 and 1.9 ppm (4H or 12H int.) |
| Thioureas T21 to T24: | signal at 7.00 ppm (1H integ.) |

EXAMPLE 19

0.01 mole of thiourea T8 in solution in a minimum of chloroform and 0.05 moles of methyl iodide are introduced into a reactor equipped with a magnetic stirrer and a condenser, and the mixture is then heated at 60° C. for one hour. A white precipitate is then seen. The chloroform is then evaporated off and the residue is washed abundantly with ether and then filtered off.

A white solid is thus obtained, which is the salt of formula

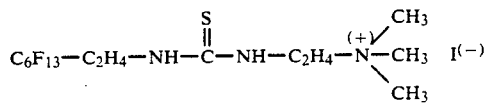

which melts at 97° C. Yield: 97%.

The surface tension of an aqueous solution containing 0.1% of this salt is 19.2 mN m$^{-1}$ at 25° C. The interfacial tension of an aqueous solution containing 0.1% of this salt, in equilibrium with cyclohexane, is 5.8 mN m$^{-1}$ at 25° C.

By proceeding in the same way with thiourea T9, the following salt

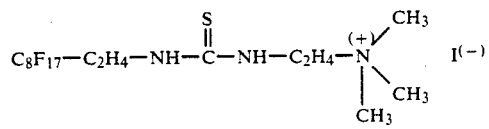

which melts at 93° C., is obtained in a 96% yield.

The surface tension of an aqueous solution containing 0.1% of this salt is 15.5 mN m$^{-1}$ at 25° C. The interfacial tension of an aqueous solution containing 0.1% of this salt, in equilibrium with cyclohexane, is 6.4 mN m.-1 at 25° C.

EXAMPLE 20

0.01 mole of thiourea T8 in solution in a minimum of chloroform and 0.01 mole of one of the quaternizing agents R-Br referred to in the first column of Table 5 below are introduced into a reactor equipped with a magnetic stirrer and a condenser. The mixture is then heated at 60° C. for 2 hours and the chloroform is then evaporated off and the residue is washed abundantly with ethyl ether.

This yields the corresponding quaternary salts of formula:

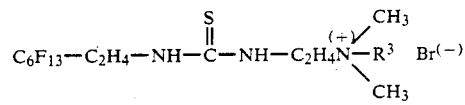

which are colorless or slightly orange-colored pastes. These salts are completely water-soluble. Their yield and the surface tension at 25° C. of an aqueous solution at a concentration of 0.1% are shown in the second and third columns of Table 5.

TABLE 5

| Quaternizing agent R$^3$—Br | Yield (%) | $\gamma$s (mN m$^{-1}$) |
|---|---|---|
| HOC$_2$H$_4$—Br | 70 | 15.4 |
| CH$_2$=CH—CH$_2$—Br | 95 | 16.4 |
| 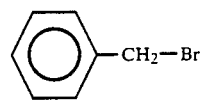 | 95 | 17.4 |

EXAMPLE 21

By starting with the aliphatic bromides C$_n$H$_{2n+1}$Br referred to in the second column of Table 6 below and with thioureas of formula:

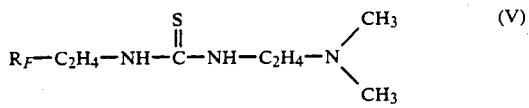

whose perfluoroalkyl radical $R_F$ is referred to in the first column of Table 6, the salts of formula:

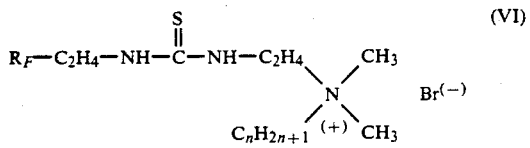

were prepared by the following procedure:

0.01 mole of thiourea (V) in solution in a minimum of chloroform and 0.01mole of aliphatic bromide $C_nH_{2n+1}Br$ are introduced into a reactor equipped with a magnetic stirrer and a condenser and the mixture is then heated in refluxing chloroform for 96 hours. The chloroform is then evaporated off and the residue is washed abundantly with petroleum ether to remove the impurities and to precipitate the ammonium salt of formula (VI) which, after removal of the petroleum ether, in most cases takes the form of a colorless paste.

However, if precipitation of the quaternary salt (VI) in petroleum ether presents difficulties, the mixture must be cooled to 0° C. for a few hours; a translucent oil then appears, which is separated from the solvent by decanting, it being possible for the operation to be repeated once. The expected ammonium compound is then obtained in the form of a translucent oil.

The surface tension $\gamma s$ and interfacial tension $\gamma i$ (relative to cyclohexane) of the ammonium salt in question, which are measured at 25° C. in aqueous solution at a concentration of 0.1%, are shown in the fourth and fifth columns of Table 6, the third column showing the yield.

TABLE 6

| AMMONIUM SALTS OF FORMULA (VI) | | | | |
| --- | --- | --- | --- | --- |
| RF | $C_nH_{2n+1}$ | Yield (%) | $\gamma s$ (mN m$^{-1}$) | $\gamma i$ (mN m$^{-1}$) |
| $C_4F_9$ | $C_8H_{17}$ | 60 | 19.7 | 0.7 |
| $C_4F_9$ | $C_{12}H_{25}$ | 78 | 23.1 | 1.9 |
| $C_4F_9$ | $C_{16}H_{33}$ | 65 | 26.8 | 2.1 |
| $C_6F_{13}$ | $C_8H_{17}$ | 74 | 15.9 | 1.4 |
| $C_6F_{13}$ | $C_{12}H_{25}$ | 67 | 17.5 | 0.8 |
| $C_6F_{13}$ | $C_{16}H_{33}$ | 70 | 20.3 | 0.7 |
| $C_8F_{17}$ | $C_5H_{11}$ | 62 | 16 | 2 |
| $C_8F_{17}$ | $C_8H_{17}$ | 75 | 15.9 | 3.2 |
| $C_8F_{17}$ | $C_{12}H_{25}$ | 72 | 15.2 | 2.2 |

EXAMPLE 22

0.02 moles of thiourea T8 in solution in a minimum of chloroform and 0.01 mole of 1,2-dibromoethane are introduced into a reactor equipped with a magnetic stirrer and a condenser. The mixture is heated under reflux for 24 hours and the chloroform is then evaporated off and the residue is taken up with ethyl ether. The double quaternary salt precipitates. After removal of the solvent the double quaternary salt of formula:

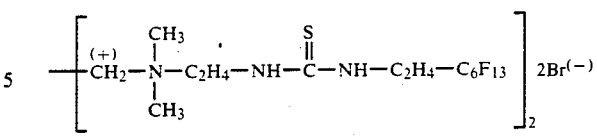

is obtained in a 75% yield.

The surface tension of an aqueous solution containing 0.1% of this salt is 15.5 mN m$^{-1}$ at 25° C. The interfacial tension in relation to cyclohexane in the same conditions is 5.5 mN m$^{-1}$.

By proceeding in the same manner starting with 1,3-dibromopropane, the double quaternary salt of formula:

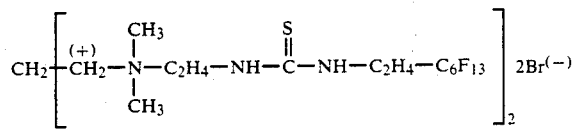

is obtained in a 98% yield. The surface tension of an aqueous solution containing 0.1% of this salt is 16.4 mN m$^{-1}$ at 25° C. The interfacial tension relative to cyclohexane in the same conditions is 7.7 mN m$^{1}$.

EXAMPLE 23

0.01 mole of thiourea T8 dissolved in a minimum of tetrahydrofuran is introduced into a reactor equipped with a magnetic stirrer and a condenser and aqueous hydrogen peroxide is then added in excess (20%). The mixture is then heated at 40° C. with stirring for 3 hours and is then left for twelve hours at room temperature. A small quantity of water (approximately 1 ml) is then added and the mixture is heated to 40° C. for 15 minutes.

The tetrahydrofuran is then evaporated off and the residue is taken up with methanol and then filtered. The filtrate is then evaporated off and a beige pasty solid which is the N-oxide of formula:

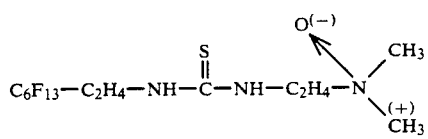

is obtained in a 65% yield.

The surface tension of an aqueous solution containing 0.1% of this N-oxide at 25° C. is 16.3 mN m$^{-1}$

EXAMPLE 24

0.01 mole of thiourea T8 and 25 ml of isopropanol are introduced into a reactor equipped with a magnetic stirrer and a condenser and a solution of 1.25 g of sodium chloroacetate in 25 ml isopropanol is then added. The mixture is then heated at 90° C. for 20 hours, the solvent is evaporated off and the residue is taken up with ethyl ether. After removal of the liquid phase, the pasty solid obtained is washed with methanol and the filtrate is evaporated to dryness. A pasty white solid which is the betaine of formula:

$$C_6F_{13}-C_2H_4-NH-\overset{S}{\overset{\|}{C}}-NH-C_2H_4-\overset{CH_3}{\underset{\underset{CH_2CO_2}{|}}{\overset{(+)}{N}}-CH_3}$$

is thus obtained in a 65% yield.

The surface tension of an aqueous solution containing 1 0.1% of this betaine is 16.2 mN m$^{-1}$.

The preceding references are hereby incorporated by reference.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Polyfluoroalkyl nitrogen compounds, comprising those corresponding to the formula:

$$R_F(CH_2)_2-X$$

wherein X is a thiourea group —NH—CS—A and A is chosen from the groups (A1) to (A5) of formulae:

$$-NH_2 \quad (A1)$$

$$-N\begin{matrix}R^1\\R^2\end{matrix} \quad (A2)$$

$$-NH-Q-\overset{(+)}{\underset{R}{N}}-R^3 \quad Z^{(-)} \quad (A3)$$

$$-NH-Q-\overset{R^1}{\underset{R}{\overset{(+)}{N}}}-Q'-\overset{R}{\underset{R}{\overset{(+)}{N}}}-Q-NH-\overset{S}{\overset{\|}{C}}-NH-(CH_2)_2R_F \quad 2Z^{(-)} \quad (A4)$$

$$-NH-Q-\overset{(+)}{\underset{R}{N}}\overset{R}{\longrightarrow}O^{(-)} \quad (A5)$$

each of Q and Q', which are identical or different, denotes and alkylene bridge of 2 to 8 carbon atoms, R denotes an unsubstituted linear alkyl radical containing from 1 to 4 carbon atoms, R$^1$ denotes a linear or branched alkyl radical containing form 1 to 18 carbon atoms and optionally substituted, and optionally substituted aryl or aralkyl radical, and allyl, methallyl or propargyl radical, a —(CH$_2$)$_2$R$'_F$ group or a Q—NR$_2$ group, said optional substituents being selected from at least one halogen atom, a hydroxyl or mercapto group, or a sulphonate or sulfate functional group, R$^2$ denotes a hydrogen atom, an alkyl radical as defined for R$^1$ or, provided that R$^1$ is an alkyl or allyl radical, and allyl radical, R$^3$ denotes an alkyl or aralkyl radical as defined for R$^1$, an allyl, methallyl or propargyl radical, or a —CH$_2$S—(CH$_2$)$_2$—R$'_F$ group, Z(—) denotes a monovalent anion or its equivalent, and each of R$_F$ and R$'_F$, which are identical or different, denotes a linear or branched perfluoroalkyl radical containing from 2 to 16 carbon atoms.

2. Compounds according to claim 1, wherein R$^1$ is an alkyl, aryl or aralkyl radical substituted by at least one halogen atom, a hydroxyl or mercapto group, or a sulphonate or sulphate functional group.

3. Compounds according to claim 1, wherein each of the radicals R$_F$ and R$'_F$ contains from 4 to 12 carbon atoms.

* * * * *

UNITED STATES PATENT AND TRADEMARK OFFICE
CERTIFICATE OF CORRECTION

PATENT NO. : 5,026,910

DATED : June 25, 1991

INVENTOR(S) : Bollens, et. al.

It is certified that error appears in the above-identified patent and that said Letters Patent is hereby corrected as shown below:

Column 19, line 12, change "and" to --an--.

Column 19, line 17, change "and" to --an--.

Column 19, line 18, change "and" to --an--.

Column 19, line 25, change "and" to --an--.

Column 19, line 16, change "form" to --from--.

Signed and Sealed this

Twenty-sixth Day of January, 1993

Attest:

STEPHEN G. KUNIN

*Attesting Officer*  *Acting Commissioner of Patents and Trademarks*